(12) United States Patent
Yang (10) Patent No.: US 11,097,048 B2
(45) Date of Patent: Aug. 24, 2021

(54) UNILATERAL DRIVING MECHANISM FOR A PORTABLE INFUSION SYSTEM

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 324 days.

(21) Appl. No.: 16/094,700

(22) PCT Filed: Apr. 18, 2016

(86) PCT No.: PCT/CN2016/079573
§ 371 (c)(1),
(2) Date: Oct. 18, 2018

(87) PCT Pub. No.: WO2017/181324
PCT Pub. Date: Oct. 26, 2017

(65) Prior Publication Data
US 2019/0117881 A1    Apr. 25, 2019

(51) Int. Cl.
| | | |
|---|---|---|
| *A61M 5/142* | (2006.01) | |
| *A61M 5/315* | (2006.01) | |
| *A61M 5/145* | (2006.01) | |
| *A61M 5/168* | (2006.01) | |
| *A61M 5/14* | (2006.01) | |

(52) U.S. Cl.
CPC .......... *A61M 5/142* (2013.01); *A61M 5/1452* (2013.01); *A61M 5/14244* (2013.01); *A61M 5/16804* (2013.01); *A61M 5/31576* (2013.01); *A61M 5/14* (2013.01); *A61M 2005/14208* (2013.01); *A61M 2005/14533* (2013.01)

(58) Field of Classification Search
CPC .......... A61M 5/31593; A61M 5/31581; A61M 5/31576; A61M 2205/0266; A61M 5/1452; A61M 2005/14506; A61M 2005/14533; A61M 5/16804; A61M 5/14244; A61M 5/142
See application file for complete search history.

(56) References Cited

U.S. PATENT DOCUMENTS 6,684,724 B2 * 2/2004 Narasimhiah .......... F03G 7/065
74/112

FOREIGN PATENT DOCUMENTS

| CN | 102233148 A | 11/2011 |
|---|---|---|
| CN | 103458941 A | 12/2013 |
| CN | 103463695 A | 12/2013 |
| CN | 103830785 A | 6/2014 |

(Continued)

*Primary Examiner* — Nathan R Price
*Assistant Examiner* — Melissa A Snyder
(74) *Attorney, Agent, or Firm* — JCIP Global Inc.

(57) ABSTRACT

A unilateral driving mechanism for a portable infusion system is provided. The unilateral driving mechanism comprises an actuator (1), a swinging part (2), gears (4), blockers (5), a compression spring (6), a rod (7), a reservoir (8), a plunger (9) and a control circuit. One end of the rod (7) is connected with the gears (4), the other end of the rod (7) is connected with the plunger (9), and one lower limb of the swinging part (2) is connected with the spring (6). The unilateral driving mechanism for a portable infusion system has advantages of compact structure, small volume, low power consumption, low cost, high precision and convenience in use.

16 Claims, 3 Drawing Sheets

(56) References Cited

FOREIGN PATENT DOCUMENTS

| EP | 1066846 A1 | 1/2001 |
|----|----|----|
| WO | WO 2014036308 A2 | 3/2014 |
| WO | WO 2015104412 A1 | 7/2015 |

* cited by examiner

UNILATERAL DRIVING MECHANISM FOR A PORTABLE INFUSION SYSTEM

TECHNICAL FIELD

The present invention generally relates to the field of medical appliance, specifically to a unilateral driving mechanism for a portable infusion system.

BACKGROUND OF THE INVENTION

Currently, drug infusion products majorly realize administration by combining motors and transmission mechanism, which has disadvantages as complex structure, large volume, high power consumption, low precision, high cost, difficult maintenance and inconvenience in using of the drug infusion product. Moreover, the power output from motor operation usually needs to be converted into the driving force of the push rod to realize administration by a decelerator or a driving thread of an output shaft of a decelerator, during whose process a series of movements take place, so the functioning of the motor cannot always guarantee the normal operation of the push rod and the accuracy of the administration, which causes safety risks.

Furthermore, incidents of abnormal flow rate control of the products in the current market have been occurring from time to time. According to the statistics obtained from the reports received by the National Adverse Drug Reaction Monitoring Center of China in the recent 8 years, infusion pump performance anomalies accounted for 38% of all suspected medical device adverse events with the main problems including abnormal flow rate control, drug pumping failures, infusion tube leakage, etc, among which abnormal flow rate control accounted for 28% of the total adverse event reports. Ultra high flow rate may cause an overdose and toxicity; and ultra low flow rate may result in doses too small to reach any therapeutic effect. One of the most likely reasons for inaccurate control of the flow rate is the imperfect design of the monitoring system, and the products in the current market have not reached the level of accurate control of the flow rate.

Therefore, a small, low cost, lightweight, and easy-to-use alternative of driving mechanism with a reliable and effective way to monitor the administration, is playing a very important role in ensuring that the portable infusion system realizes accurate administration in accordance with the requirements.

SUMMARY OF THE INVENTION

Regarding the above-mentioned shortcomings of the prior art, the present invention provides a unilateral driving mechanism for a portable infusion system, to solve the problems including large volume, high power consumption, high cost, inconvenience in using and low precision in controlling administration of the driving mechanism in prior arts.

The unilateral driving mechanism for a portable infusion system in the present invention can be realized in the following way, comprising:

An actuator, a swinging part, gears, blockers, a tension spring, a rod, a reservoir, and a plunger;

One end of the rod is connected with the gears, the other end of the rod is connected with the plunger, one lower limb of the swinging part is connected with the tension spring;

When there is no unilateral drive applied, the tension spring is in its initial state, and the other lower limb of the swinging part which is not connected with the tension spring is separated from the blocker;

When there is a unilateral drive applied on the actuator, the head of the swinging part is driven and drives the swinging part swinging forward once around its central axis, and one upper limb of the swinging part rotates one gear to push the plunger in the reservoir to administrate fluid in the reservoir to the patient by one unit dose; at the same time, the other lower limb of the swinging part which is not connected with the tension spring contacts the blocker, and the tension spring is in its stretched state;

When the unilateral drive applied on the actuator is withdrawn, the tension spring is released, and the tension from releasing the tension spring drives the swinging part swinging backward once around its central axis, and the other upper limb of the swinging part rotates the other gear to push the plunger in the reservoir to administrate fluid in the reservoir to the patient by one unit dose; at the same time, the lower limb of the swinging part which is not connected with the tension spring is separated from the blocker;

Applying an one-time unilateral drive on the actuator makes the swinging part swings once forward and once backward, which leads to the administration of two unit doses of fluid to the patient by the infusion system; applying unilateral drive on the actuator at regular intervals makes the infusion system realize continuous administration.

The unilateral driving mechanism for a portable infusion system in the present invention can further be realized in the following way, comprising:

An actuator, a swinging part, gears, blockers, a compression spring, a rod, a reservoir, and a plunger;

One end of the rod is connected with the gears, the other end of the rod is connected with the plunger, one lower limb of the swinging part is connected with the compression spring;

When there is no unilateral drive applied, the compression spring is in its initial state, and the other lower limb of the swinging part which is not connected with the compression spring contacts the blocker;

When there is a unilateral drive applied on the actuator, the head of the swinging part is driven and drives the swinging part swinging forward once around its central axis, and one upper limb of the swinging part rotates one gear to push the plunger in the reservoir to administrate fluid in the reservoir to the patient by one unit dose; at the same time, the lower limb of the swinging part which is not connected with the compression spring is separated from the blocker, and the compression spring is in its compressed state;

When the unilateral drive applied on the actuator is withdrawn, the compression spring is released, and the tension from releasing the compression spring drives the swinging part swinging backward once around its central axis, and the other upper limb of the swinging part rotates the other gear to push the plunger in the reservoir to administrate fluid in the reservoir to the patient by one unit dose; at the same time, the lower limb of the swinging part which is not connected with the compression spring contacts the blocker again;

Applying an one-time unilateral drive on the actuator makes the swinging part swings once forward and once backward, which leads to the administration of two unit doses of fluid to the patient by the infusion system; applying unilateral drive on the actuator at regular intervals makes the infusion system realize continuous administration.

The unilateral driving mechanism for a portable infusion system in the present invention can further be realized in the following way, comprising:

An actuator, a swinging part, gears, blockers, a torsion spring, a rod, a reservoir, and a plunger;

One end of the rod is connected with the gears, the other end of the rod is connected with the plunger, one lower limb of the swinging part is connected with the torsion spring;

When there is no unilateral drive applied, the torsion spring is in its initial state, and the other lower limb of the swinging part which is not connected with the torsion spring contacts the blocker;

When there is a unilateral drive applied on the actuator, the head of the swinging part is driven and drives the swinging part swinging forward once around its central axis, and one upper limb of the swinging part rotates one gear to push the plunger in the reservoir to administrate fluid in the reservoir to the patient by one unit dose; at the same time, the other lower limb of the swinging part which is not connected with the torsion spring is separated from the blocker, and the torsion spring is in its twisted state;

When the unilateral drive applied on the actuator is withdrawn, the torsion spring is released, and the torque from releasing the torsion spring drives the swinging part swinging backward once around its central axis, and the other upper limb of the swinging part rotates the other gear to push the plunger in the reservoir to administrate fluid in the reservoir to the patient by one unit dose; at the same time, the other lower limb of the swinging part which is not connected with the torsion spring contacts the blocker again;

Applying an one-time unilateral drive on the actuator makes the swinging part swing once forward and once backward, which leads to the administration of two unit doses of fluid to the patient by the infusion system; applying unilateral drive on the actuator at regular intervals makes the infusion system realize continuous administration.

For the purpose of monitoring the administration of the infusion system, a monitoring element configured to monitor the movement of the swinging part and a control circuit are further set on the blocker.

Each time the swinging part contacts the blocker, the monitoring element recognizes the movement of the swinging part and sends a signal to a control unit of the portable infusion system via the control circuit to monitor the administration of the system.

Alternatively, the monitoring element is a metallic element.

Alternatively, the monitoring element is an optical element.

Alternatively, each time a unilateral drive is applied on the actuator, the unit dose administered by the portable infusion system is 0.05-5 ul;

Alternatively, the unilateral driving mechanism for a portable infusion system in the present invention further comprises a wire, by which the actuator is connected with the head of the swinging part.

Alternatively, the actuator is a piezoelectric actuator.

Alternatively, the actuator is a magnet actuator.

Alternatively, the actuator is a gas actuator.

Alternatively, the actuator is a chemical actuator.

Alternatively, the actuator is a shape memory alloy.

Alternatively, the actuator is a wax actuator.

Compared to prior arts, the unilateral driving mechanism for a portable infusion system in the present invention has advantages in the following ways:

The unilateral driving mechanism for a portable infusion system in the present invention has features of compact structure, small volume, low power consumption, low cost, high precision, and convenience in using. Each time a unilateral drive is applied on the actuator, the swinging part firstly swings once forward, then the tension from releasing the spring from its stretched, compressed or twisted state is turned into the driving force for administration, making the swinging part swing once backward, that is to say, when the unilateral drive is applied once, the infusion system can realize administration by two unit doses. Moreover, the unilateral driving mechanism for a portable infusion system in the present invention can monitor the operation of the swinging part in real time to ensure the safety of the infusion system and further enhance the performance of the infusion system. Once the swinging part is not in proper contact with the blocker and a signal is not sent to the control unit according to the set program by the monitoring element on the blocker, the administration will be suspended and the error will not exceed a single unit of dose.

DETAILED DESCRIPTION

To make the above-mentioned objects, features and advantages of the present invention more obvious and understandable, the embodiments of the present invention are described in the following through specific embodiments.

EMBODIMENT1

Figure 1:
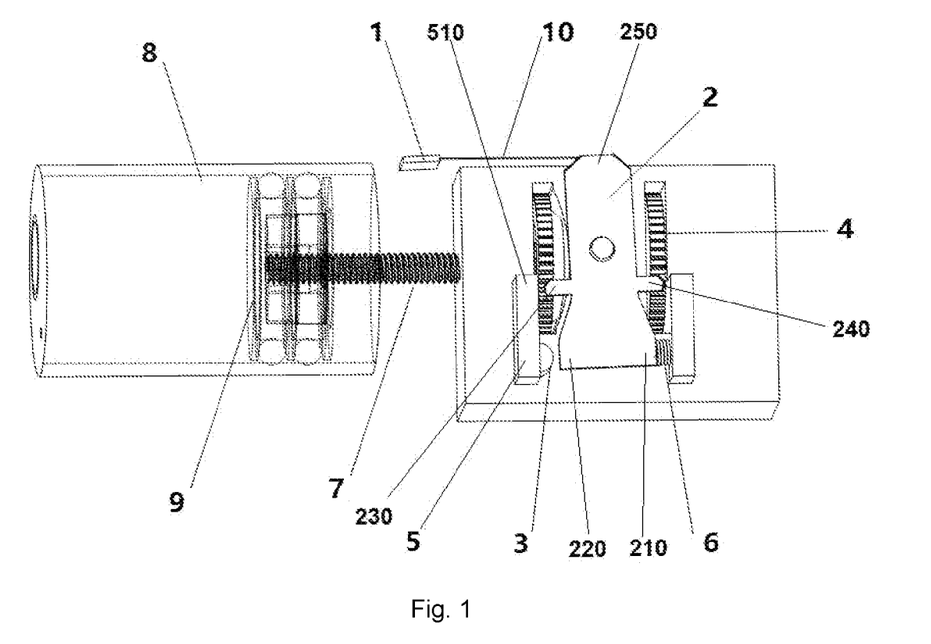
FIG. 1 illustrates the schematic diagram of a unilateral driving mechanism for a portable infusion system using a tension spring.

Referring to the FIG. 1, provided is an exemplary embodiment of a unilateral driving mechanism for a portable infusion system in the present invention, comprising:

An actuator 1, a swinging part 2, gears 4, blockers 5, a tension spring 6, a rod 7, a reservoir 8, a plunger 9, and a wire 10;

The actuator 1 is connected with the swinging part 2 by the wire 10, one end of the rod 7 is connected with the gears 4, the other end of the rod 7 is connected with the plunger 9, a first lower limb 210 of the swinging part 2 is connected with the tension spring 6; a monitoring element 3 configured to monitor the movement of the swinging part 2 and a control circuit 510 are further set on the blocker 5;

When there is no unilateral drive applied, the tension spring 6 is in its initial state, and a second lower limb 220 of the swinging part 2 which is not connected with the tension spring 6 is separated from the blocker 5;

When there is a unilateral drive applied on the actuator 1, a head 250 of the swinging part 2 is pulled by the wire 10 and drives the swinging part 2 to swing forward once around its central axis, and a first upper limb 230 of the swinging part 2 rotates one gear 4 which then moves the rod 7 to push the plunger 9 in the reservoir 8 to administrate fluid in the reservoir 8 to the patient by one unit dose when the tension spring 6 is in its stretched state; at the same time, the second lower limb 220 of the swinging part 2 which is not connected with the tension spring 6 contacts the blocker 5, and the monitoring element 3 recognizes the movement of the swinging part 2 and sends a signal to the control unit via the control circuit 510;

When the unilateral drive applied on the actuator 1 is withdrawn, the tension spring 6 is released, and the tension from releasing the tension spring 6 drives the swinging part 2 to swing backward once around its central axis, and a second upper limb 240 of the swinging part 2 rotates the other gear 4 which then moves the rod 7 to push the plunger 9 in the reservoir 8 to administrate fluid in the reservoir 8 to the patient by one unit dose; at the same time, the second lower limb 220 of the swinging part 2 which is not connected with the tension spring 6 is separated from the blocker 5;

When an one-time unilateral drive is applied on the actuator 1, the swinging part 2 swings once forward, then the tension from releasing the tension spring 6 from its stretched state is turned into the driving force for administration, making the swinging part 2 swing once backward, so the infusion system can realize administration by two unit doses; applying unilateral drive on the actuator 1 at regular intervals makes the infusion system realize continuous administration, and each time the swinging part 2 contacts the blocker 5, the monitoring element 3 sends a signal to the control unit via the control circuit 510 to monitor the administration of the system constantly.

EMBODIMENT2

Figure 2:
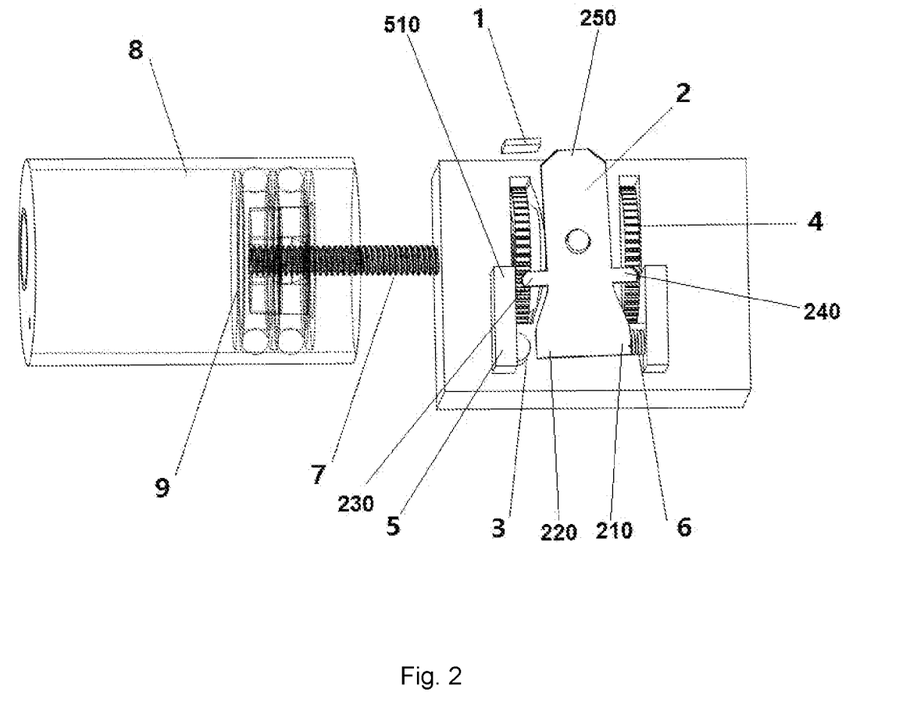
FIG. 2 illustrates the schematic diagram of a unilateral driving mechanism for a portable infusion system using one of multiple actuators comprising a piezoelectric actuator, a magnet actuator, a gas actuator, a chemical actuator or a wax actuator along with a compression spring.

Referring to the FIG. 2, also provided is an exemplary embodiment of a unilateral driving mechanism for a portable infusion system in the present invention, comprising:

An actuator 1, a swinging part 2, gears 4, blockers 5, a compression spring 6, a rod 7, a reservoir 8, and a plunger 9;

The actuator 1 is a piezoelectric actuator, one end of the rod 7 is connected with the gears 4, the other end of the rod 7 is connected with the plunger 9, a first lower limb 210 of the swinging part 2 is connected with the compression spring 6; a monitoring element 3 configured to monitor the movement of the swinging part 2 and a control circuit 510 are further set on the blocker 5, and the monitoring element 3 is a metallic element;

When there is no piezoelectric drive applied, the compression spring 6 is in its initial state, and a second lower limb 220 of the swinging part 2 which is not connected with the compression spring 6 contacts the blocker 5;

When there is a piezoelectric drive applied on the piezoelectric actuator, the film on the piezoelectric actuator generates a vertical pressure and pushes a head 250 of the swinging part 2, driving the swinging part 2 to swing forward once around its central axis, and a first upper limb 230 of the swinging part 2 rotates one gear 4 which then moves the rod 7 to push the plunger 9 in the reservoir 8 to administrate fluid in the reservoir 8 to the patient by one unit dose; at the same time, the second lower limb 220 of the swinging part 2 which is not connected with the compression spring 6 is separated from the blocker 5, and the compression spring 6 is in its compressed state;

When the piezoelectric drive applied on the piezoelectric actuator is withdrawn, the compression spring 6 is released, and the tension from releasing the compression spring 6 drives the swinging part 2 to swing backward once around its central axis, and a second upper limb 240 of the swinging part 2 rotates the other gear 4 which then moves the rod 7 to push the plunger 9 in the reservoir 8 to administrate fluid in the reservoir 8 to the patient by one unit dose; at the same time, the second lower limb 220 of the swinging part 2 which is not connected with the compression spring 6 contacts the blocker 5 again; the metallic element recognizes the movement of the swinging part 2 and sends a signal to the control unit via the control circuit 510;

When an one-time piezoelectric drive is applied on the piezoelectric actuator, the swinging part 2 swings once forward, then the tension from releasing the compression spring 6 from its compressed state is turned into the driving force for administration, making the swinging part 2 swing once backward, so the infusion system can realize administration by two unit doses; applying piezoelectric drive on the piezoelectric actuator at regular intervals makes the infusion system realize continuous administration, and each time the swinging part 2 contacts the blocker 5, the metallic element sends a signal to the control unit via the control circuit 510 to monitor the administration of the system constantly.

EMBODIMENT3

Referring again to the FIG. 2, also provided is an exemplary embodiment of a unilateral driving mechanism for a portable infusion system in the present invention, comprising:

An actuator 1, a swinging part 2, gears 4, blockers 5, a compression spring 6, a rod 7, a reservoir 8, and a plunger 9;

The actuator 1 is a magnet actuator, one end of the rod 7 is connected with the gears 4, the other end of the rod 7 is connected with the plunger 9, a first lower limb 210 of the swinging part 2 is connected with the compression spring 6; a monitoring element 3 configured to monitor the movement of the swinging part 2 and a control circuit 510 are further set on the blocker 5, and the monitoring element 3 is a metallic element;

When there is no magnet drive applied, the compression spring 6 is in its initial state, and a second lower limb 220 of the swinging part 2 which is not connected with the compression spring 6 contacts the blocker 5;

When there is a magnet drive applied on the magnet actuator, the magnet actuator generates a magnetic attraction on a head 250 of the swinging part 2, moving the head 250 of the swinging part 2 towards the magnet actuator, making the swinging part 2 swing forward once around its central axis, and a first upper limb 230 of the swinging part 2 rotates one gear 4 which then moves the rod 7 to push the plunger 9 in the reservoir 8 to administrate fluid in the reservoir 8 to the patient by one unit dose; at the same time, the second lower limb 220 of the swinging part 2 which is not connected with the compression spring 6 is separated from the blocker 5, and the compression spring 6 is in its compressed state;

When the magnet drive applied on the magnet actuator is withdrawn, the compression spring 6 is released, and the tension from releasing the compression spring 6 drives the swinging part 2 to swing backward once around its central axis, and a second upper limb 240 of the swinging part 2 rotates the other gear 4 which then moves the rod 7 to push the plunger 9 in the reservoir 8 to administrate fluid in the reservoir 8 to the patient by one unit dose; at the same time, the second lower limb 220 of the swinging part 2 which is not connected with the compression spring 6 contacts the blocker 5 again; the metallic element recognizes the movement of the swinging part 2 and sends a signal to a control unit via the control circuit 510;

When an one-time magnet drive is applied on the magnet actuator, the swinging part 2 swings once forward, then the tension from releasing the compression spring 6 from its compressed state is turned into the driving force for administration, making the swinging part 2 swing once backward, so the infusion system can realize administration by two unit doses; applying magnet drive on the magnet actuator at regular intervals makes the infusion system realize continuous administration, and each time the swinging part 2 contacts the blocker 5, the metallic element sends a signal to the control unit via the control circuit 510 to monitor the administration of the system constantly.

EMBODIMENT4

Referring again to the FIG. 2, also provided is an exemplary embodiment of a unilateral driving mechanism for a portable infusion system in the present invention, comprising:

An actuator 1, a swinging part 2, gears 4, blockers 5, a compression spring 6, a rod 7, a reservoir 8, and a plunger 9;

The actuator 1 is a gas actuator, one end of the rod 7 is connected with the gears 4, the other end of the rod 7 is connected with the plunger 9, a first lower limb 210 of the swinging part 2 is connected with the compression spring 6; a monitoring element 3 configured to monitor the movement of the swinging part 2 and a control circuit 510 are further set on the blocker 5, and the monitoring element 3 is a metallic element;

When there is no gas drive applied, the compression spring 6 is in its initial state, and a second lower limb 220 of the swinging part 2 which is not connected with the compression spring 6 contacts the blocker 5;

When there is a gas drive applied on the gas actuator, the gas actuator pushes a head 250 of the swinging part 2, making the swinging part 2 swinging forward once around its central axis, and a first upper limb 230 of the swinging part 2 rotates one gear 4 which then moves the rod 7 to push the plunger 9 in the reservoir 8 to administrate fluid in the reservoir 8 to the patient by one unit dose; at the same time, the second lower limb 220 of the swinging part 2 which is not connected with the compression spring 6 is separated from the blocker 5, and the compression spring 6 is in its compressed state;

When the gas drive applied on the gas actuator is withdrawn, the compression spring 6 is released, and the tension from releasing the compression spring 6 drives the swinging part 2 to swing backward once around its central axis, and a second upper limb 240 of the swinging part 2 rotates the other gear 4 which then moves the rod 7 to push the plunger 9 in the reservoir 8 to administrate fluid in the reservoir 8 to the patient by one unit dose; at the same time, the second lower limb 220 of the swinging part 2 which is not connected with the compression spring 6 contacts the blocker 5 again; the metallic element recognizes the movement of the swinging part 2 and sends a signal to a control unit via the control circuit 510;

Applying one time gas drive on the gas actuator, the swinging part 2 firstly swings once forward, then the tension from releasing the compression spring 6 from its compressed state is turned into the driving force for administration, making the swinging part 2 swing once backward, so the infusion system can realize administration by two unit doses; applying gas drive on the gas actuator at regular intervals makes the infusion system realize continuous administration, and each time the swinging part 2 contacts the blocker 5, the metallic element sends a signal to the control unit via the control circuit 510 to monitor the administration of the system constantly.

EMBODIMENT5

Referring again to the FIG. 2, also provided is an exemplary embodiment of a unilateral driving mechanism for a portable infusion system in the present invention, comprising:

An actuator 1, a swinging part 2, gears 4, blockers 5, a compression spring 6, a rod 7, a reservoir 8, and a plunger 9;

The actuator 1 is a chemical actuator, one end of the rod 7 is connected with the gears 4, the other end of the rod 7 is connected with the plunger 9, a first lower limb 210 of the swinging part 2 is connected with the compression spring 6; a monitoring element 3 configured to monitor the movement of the swinging part 2 and a control circuit 510 are further set on the blocker 5, and the monitoring element 3 is a metallic element;

When there is no chemical drive applied, the compression spring 6 is in its initial state, and a second lower limb 220 of the swinging part 2 which is not connected with the compression spring 6 contacts the blocker 5;

When there is a chemical drive applied on the chemical actuator, the chemical actuator pushes a head 250 of the swinging part 2, drying the swinging part 2 to swing forward once around its central axis, and a first upper limb 230 of the swinging part 2 rotates one gear 4 which then moves the rod 7 to push the plunger 9 in the reservoir 8 to administrate fluid in the reservoir 8 to the patient by one unit dose; at the same time, the second lower limb 220 of the swinging part 2 which is not connected with the compression spring 6 is separated from the blocker 5, and the compression spring 6 is in its compressed state;

When the chemical drive applied on the chemical actuator is withdrawn, the compression spring 6 is released, and the tension from releasing the compression spring 6 drives the swinging part 2 to swing backward once around its central axis, and a second upper limb 240 of the swinging part 2 rotates the other gear 4, which moves the rod 7 to push the plunger 9 in the reservoir 8 to administrate fluid in the reservoir 8 to the patient by one unit dose; at the same time, the second lower limb 220 of the swinging part 2 which is not connected with the compression spring 6 contacts the blocker 5 again; the metallic element recognizes the movement of the swinging part 2 and sends a signal to a control unit via the control circuit 510;

Applying one time chemical drive on the chemical actuator, the swinging part 2 firstly swings once forward, then the tension from releasing the compression spring 6 from its compressed state is turned into the driving force for administration, making the swinging part 2 swing once backward, so the infusion system can realize administration by two unit doses; applying chemical drive on the chemical actuator at regular intervals makes the infusion system realize continuous administration, and each time the swinging part 2 contacts the blocker 5, the metallic element sends a signal to the control unit via the control circuit 510 to monitor the administration of the system constantly.

EMBODIMENT6

Referring again to the FIG. 2, also provided is an exemplary embodiment of a unilateral driving mechanism for a portable infusion system in the present invention, comprising:

An actuator 1, a swinging part 2, gears 4, blockers 5, a compression spring 6, a rod 7, a reservoir 8, and a plunger 9;

The actuator 1 is a wax actuator, one end of the rod 7 is connected with the gears 4, the other end of the rod 7 is connected with the plunger 9, a first lower limb 210 of the swinging part 2 is connected with the compression spring 6; a monitoring element 3 configured to monitor the movement of the swinging part 2 and a control circuit 510 are further set on the blocker 5, and the monitoring element 3 is a metallic element;

When there is no wax actuation applied, the compression spring 6 is in its initial state, and a second lower limb 220 of the swinging part 2 which is not connected with the compression spring 6 contacts the blocker 5;

When there is a wax actuation applied on the wax actuator, the wax actuator pushes a head 250 of the swinging part 2, driving the swinging part 2 to swing forward once around its central axis, and a first upper limb 230 of the swinging part 2 rotates one gear 4 which then moves the rod 7 to push the plunger 9 in the reservoir 8 to administrate fluid in the reservoir 8 to the patient by one unit dose; at the same time, the second lower limb 220 of the swinging part 2 which is not connected with the compression spring 6 is separated from the blocker 5, and the compression spring 6 is in its compressed state;

When the wax actuation applied on the wax actuator is withdrawn, the compression spring 6 is released, and the tension from releasing the compression spring 6 drives the swinging part 2 to swing backward once around its central axis, and a second upper limb 240 of the swinging part 2 rotates the other gear 4, which moves the rod 7 to push the plunger 9 in the reservoir 8 to administrate fluid in the reservoir 8 to the patient by one unit dose; at the same time, the second lower limb 220 of the swinging part 2 which is not connected with the compression spring 6 contacts the blocker 5 again; the metallic element recognizes the movement of the swinging part 2 and sends a signal to a control unit via the control circuit 510;

Applying one time wax actuation on the wax actuator, the swinging part 2 firstly swings once forward, then the tension from releasing the compression spring 6 from its compressed state is turned into the driving force for administration, making the swinging part 2 swing once backward, so the infusion system can realize administration by two unit doses; applying wax actuation on the wax actuator at regular intervals makes the infusion system realize continuous administration, and each time the swinging part 2 contacts the blocker 5, the metallic element sends a signal to the control unit via the control circuit 510 to monitor the administration of the system constantly.

EMBODIMENT7

Figure 3:
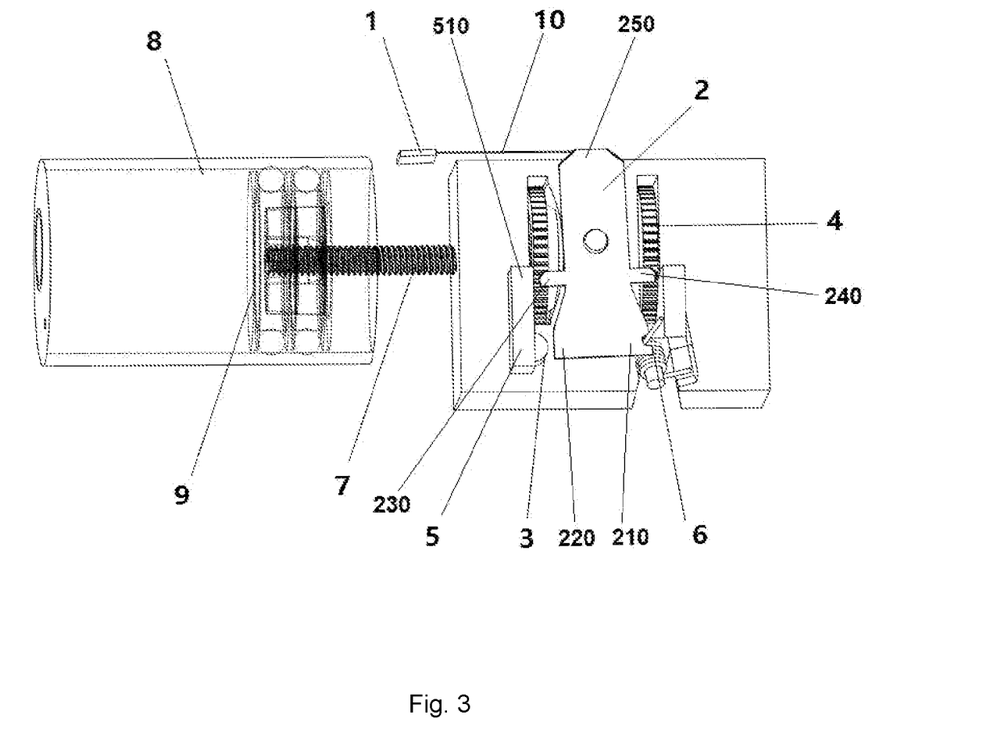
FIG. 3 illustrates the schematic diagram of a unilateral driving mechanism for a portable infusion system using a shape memory alloy and a torsion spring.

Referring to the FIG. 3, also provided is an exemplary embodiment of a unilateral driving mechanism for a portable infusion system in the present invention, comprising:

An actuator 1, a swinging part 2, gears 4, blockers 5, a torsion spring 6, a rod 7, a reservoir 8, a plunger 9, a wire 10;

The actuator 1 is a shape memory alloy which is connected with the swinging part 2 by the wire 10, one end of the rod 7 is connected with the gears 4, the other end of the rod 7 is connected with the plunger 9, a first lower limb 210 of the swinging part 2 is connected with the torsion spring 6; a monitoring element 3 configured to monitor the movement of the swinging part 2 and a control circuit 510 are further set on the blocker 5, and the monitoring element 3 is an optical element;

When there is no unilateral drive applied, the torsion spring 6 is in its initial state, and a second lower limb 220 of the swinging part 2 which is not connected with the torsion spring 6 contacts the blocker 5;

When there is a unilateral drive applied on the shape memory alloy, a head 250 of the swinging part 2 is pulled by the wire 10, making the swinging part 2 swinging forward once around its central axis, and a first upper limb 230 of the swinging part 2 rotates one gear 4 which then moves the rod 7 to push the plunger 9 in the reservoir 8 to administrate fluid in the reservoir 8 to the patient by one unit dose; at the same time, the second lower limb 220 of the swinging part 2 which is not connected with the torsion spring 6 is separated from the blocker 5, and the torsion spring 6 is in its twisted state;

When the unilateral drive applied on the shape memory alloy is withdrawn, the torsion spring 6 is released, and the torque from releasing the torsion spring 6 drives the swinging part 2 swinging backward once around its central axis, and a second upper limb 240 of the swinging part 2 rotates the other gear 4 which then moves the rod 7 to push the plunger 9 in the reservoir 8 to administrate fluid in the reservoir 8 to the patient by one unit dose; at the same time, the second lower limb 220 of the swinging part 2 which is not connected with the torsion spring 6 contacts the blocker 5 again; the optical element recognizes the movement of the swinging part 2 and sends a signal to the control unit via the control circuit 510;

Applying one time unilateral drive on the shape memory alloy, the swinging part 2 swings once forward, then the torque from releasing the torsion spring 6 from its twisted state is turned into the driving force for administration, making the swinging part 2 swing once backward, so the infusion system can realize administration by two unit doses; applying unilateral drive on the shape memory alloy at regular intervals makes the infusion system realize continuous administration, and each time the swinging part 2 contacts the blocker 5, the optical element sends a signal to the control unit via the control circuit 510 to monitor the administration of the system constantly.

The above descriptions of the detailed embodiments are only to illustrate the principle and the effect of the present invention, and it is not to limit the scope of the present invention. Those skilled in the art can modify or change the embodiments without departing from the spirit and scope of the present invention. Accordingly, all equivalent modifications and variations completed by persons of ordinary skill in the art, without departing from the spirit and technical idea of the present invention, should fall within the scope of the present disclosure defined by the appended claims.

What is claimed is:

1. A unilateral driving mechanism for a portable infusion system, comprising
    an actuator (1), a swinging part (2), gears (4), blockers (5), a tension spring (6), a rod (7), a reservoir (8), and a plunger (9);
    wherein the swinging part comprises a first lower limb (210), a second lower limb (220), a head (250), a first upper limb (230), and a second upper limb (240), wherein the tension spring (6) comprises an initial state and a stretched state, wherein
    the rod (7) comprises a first end and a second end, the first end of the rod (7) is connected with the gears (4), the second end of the rod (7) is connected with the plunger (9), and the first lower limb (210) of the swinging part (2) is connected with the tension spring (6);
    the actuator (1) is configured such that
    prior to application of a unilateral drive on the actuator (1), the tension spring (6) is in the initial state, and the second lower limb (220) of the swinging part (2), which is not connected with the tension spring (6) is separated from the blocker (5);
    upon application of the unilateral drive on the actuator (1), the head (250) of the swinging part (2) is driven and drives the swinging part (2) swinging forward once around a central axis of the swinging part, and the first upper limb (230) of the swinging part (2) rotates one of said gears (4) to push the plunger (9) in the reservoir (8) to administrate a fluid in the reservoir (8) to a patient by one unit dose; at the same time, the second lower limb (220) of the swinging part (2) which is not connected with the tension spring (6) contacts one of said blockers (5), and the tension spring (6) is in the stretched state;
    upon withdrawal of the unilateral drive on the actuator (1), the tension spring (6) is released, a tension from releasing the tension spring (6) drives the swinging part (2) swinging backward once around the central axis of the swinging part, and the second upper limb (240) of the swinging part (2) rotates a second of said gears (4) to push the plunger (9) in the reservoir (8) to administrate the fluid in the reservoir (8) to the patient by one unit dose; at the same time, the second lower limb (220) of the swinging part (2) which is not connected with the tension spring (6) is separated from one of said blockers (5);
    wherein a single application of the unilateral drive on the actuator (1) makes the swinging part (2) swing once forward and once backward, which leads to an administration of two unit doses of the fluid from the reservoir to the patient by the infusion system; applying the unilateral drive on the actuator (1) at regular intervals makes the infusion system realize continuous administration.

2. A unilateral driving mechanism for a portable infusion system, comprising
    an actuator (1), a swinging part (2), gears (4), blockers (5), a compression spring (6), a rod (7), a reservoir (8), and a plunger (9);
    wherein the swinging part comprises a first lower limb (210), a second lower limb (220), a head (250), a first upper limb (230), and a second upper limb (240), wherein the compression spring (6) comprises an initial state and a compressed state, wherein
    the rod (7) comprises a first end and a second end, the first end of the rod (7) is connected with the gears (4), the second end of the rod (7) is connected with the plunger (9), and the first lower limb (210) of the swinging part (2) is connected with the compression spring (6);
    the actuator (1) is configured such that
    prior to application of a unilateral drive on the actuator (1), the compression spring (6) is in the initial state, and the second lower limb (220) of the swinging part (2), which is not connected with the compression spring (6) contacts the blocker (5);
    upon application of the unilateral drive on the actuator (1), the head (250) of the swinging part (2) is driven and drives the swinging part (2) swinging forward once around a central axis of the swinging part, and the first upper limb (230) of the swinging part (2) rotates one of said gears (4) to push the plunger (9) in the reservoir (8) to administrate a fluid in the reservoir (8) to a patient by one unit dose; at the same time, the second lower limb (220) of the swinging part (2) which is not connected with the compression spring (6) is separated from one of said blockers (5), and the compression spring (6) is in the compressed state;
    upon withdrawal of the unilateral drive on the actuator (1), the compression spring (6) is released, a tension from releasing the compression spring (6) drives the swinging part (2) swinging backward once around the central axis of the swinging part, and the second upper limb (240) of the swinging part (2) rotates a second of said gears (4) to push the plunger (9) in the reservoir (8) to administrate the fluid in the reservoir (8) to the patient by one unit dose; at the same time, the second lower limb (220) of the swinging part (2) which is not connected with the compression spring (6) contacts one of said blockers (5) again;
    wherein a single application of the unilateral drive on the actuator (1) makes the swinging part (2) swing once forward and once backward, which leads to an administration of two unit doses of the fluid from the reservoir to the patient by the infusion system; applying the unilateral drive on the actuator (1) at regular intervals makes the infusion system realize continuous administration.

3. A unilateral driving mechanism for a portable infusion system, comprising
    an actuator (1), a swinging part (2), gears (4), blockers (5), a torsion spring (6), a rod (7), a reservoir (8), and a plunger (9);
    wherein the swinging part comprises a first lower limb (210), a second lower limb (220), a head (250), a first upper limb (230), and a second upper limb (240), wherein the torsion spring (6) comprises an initial state and a twisted state, wherein the rod (7) comprises a first end and a second end, the first end of the rod (7) is connected with the gears (4), the second end of the rod (7) is connected with the plunger (9), and the first lower limb (210) of the swinging part (2) is connected with the torsion spring (6);

the actuator (1) is configured such that prior to application of a unilateral drive on the actuator (1), the torsion spring (6) is in the initial state, and the second lower limb (220) of the swinging part (2), which is not connected with the torsion spring (6) contacts the blocker (5);upon application of the unilateral drive on the actuator (1), the head (250) of the swinging part (2) is driven and drives the swinging part (2) swinging forward once around a central axis of the swinging part, and the first upper limb (230) of the swinging part (2) rotates one of said gears (4) to push the plunger (9) in the reservoir (8) to administrate a fluid in the reservoir (8) to a patient by one unit dose; at the same time, the second lower limb (220) of the swinging part (2) which is not connected with the torsion spring (6) is separated from one of said blockers (5), and the torsion spring (6) is in the twisted state;

upon withdrawal of the unilateral drive on the actuator (1), the torsion spring (6) is released, a torque from releasing the torsion spring (6) drives the swinging part (2) swinging backward once around the central axis of the swinging part, and the second upper limb (240) of the swinging part (2) rotates a second of said gears (4) to push the plunger (9) in the reservoir (8) to administrate the fluid in the reservoir (8) to the patient by one unit dose; at the same time, the second lower limb (220) of the swinging part (2) which is not connected with the torsion spring (6) contacts one of said blocker (5) again;

wherein a single application of the unilateral drive on the actuator (1) makes the swinging part (2) swing once forward and once backward, which leads to an administration of two unit doses of the fluid from the reservoir to the patient by the infusion system; applying the unilateral drive on the actuator (1) at regular intervals makes the infusion system realize continuous administration.

4. A unilateral driving mechanism for a portable infusion system according to claim 1, wherein, a monitoring element (3) configured to monitor the movement of the swinging part (2) and a control circuit (510) are further set on the blocker (5);

each time the swinging part (2) contacts the blocker (5), the monitoring element (3) recognizes the movement of the swinging part (2) and sends a signal to a control unit of the portable infusion system via the control circuit (510) to monitor the administration of the system.

5. A unilateral driving mechanism for a portable infusion system according to claim 4, wherein, the monitoring element (3) is a metallic element or an optical element.

6. A unilateral driving mechanism for a portable infusion system according to claim 1, wherein, each time a unilateral drive is applied on the actuator (1), one of said two unit doses administered by the portable infusion system is 0.05-5ul.

7. A unilateral driving mechanism for a portable infusion system according to claim 1, further comprising a wire (10), by which the actuator (1) is connected with the head (250) of the swinging part (2).

8. A unilateral driving mechanism for a portable infusion system according to claim 1, wherein, the actuator (1) is a piezoelectric actuator or a magnet actuator or a gas actuator or a chemical actuator or a shape memory alloy or a wax actuator.

9. A unilateral driving mechanism for a portable infusion system according to claim 2, wherein, a monitoring element (3) configured to monitor a movement of the swinging part (2) and a control circuit (510) are further set on the blocker (5);

each time the swinging part (2) contacts the blocker (5), the monitoring element (3) recognizes the movement of the swinging part (2) and sends a signal to a control unit of the portable infusion system via the control circuit (510) to monitor the administration of the system.

10. A unilateral driving mechanism for a portable infusion system according to claim 3, wherein, a monitoring element (3) configured to monitor a movement of the swinging part (2) and a control circuit (510) are further set on the blocker (5);

each time the swinging part (2) contacts the blocker (5), the monitoring element (3) recognizes the movement of the swinging part (2) and sends a signal to a control unit of the portable infusion system via the control circuit (510) to monitor the administration of the system.

11. A unilateral driving mechanism for a portable infusion system according to claim 2, wherein, each time the unilateral drive is applied on the actuator (1), one of said two unit doses administered by the portable infusion system is 0.05-5ul.

12. A unilateral driving mechanism for a portable infusion system according to claim 3, wherein, each time the unilateral drive is applied on the actuator (1), one of said two unit doses administered by the portable infusion system is 0.05-5ul.

13. A unilateral driving mechanism for a portable infusion system according to claim 2, further comprising a wire (10), by which the actuator (1) is connected with the head (250) of the swinging part (2).

14. A unilateral driving mechanism for a portable infusion system according to claim 3, further comprising a wire (10), by which the actuator (1) is connected with the head (250) of the swinging part (2).

15. A unilateral driving mechanism for a portable infusion system according to claim 2, wherein, the actuator (1) is a piezoelectric actuator or a magnet actuator or a gas actuator or a chemical actuator or a shape memory alloy or a wax actuator.

16. A unilateral driving mechanism for a portable infusion system according to claim 3, wherein, the actuator (1) is a piezoelectric actuator or a magnet actuator or a gas actuator or a chemical actuator or a shape memory alloy or a wax actuator.

* * * * *